United States Patent [19]

Jaynes et al.

[11] Patent Number: 5,760,011
[45] Date of Patent: Jun. 2, 1998

[54] ANTIBIOTIC MACROLIDES

[75] Inventors: Burton H. Jaynes; Martin R. Jefson; Kristin M. Lundy, all of Groton, Conn.

[73] Assignee: Pfizer Inc., New York, N.Y.

[21] Appl. No.: 757,042

[22] Filed: Nov. 26, 1996

[51] Int. Cl.$^6$ .............................. A61K 31/70; C07H 17/08
[52] U.S. Cl. ................................. 514/30; 536/7.1
[58] Field of Search ................. 536/7.1, 7.4; 514/30

[56] References Cited

U.S. PATENT DOCUMENTS

| | | | |
|---|---|---|---|
| 3,975,372 | 8/1976 | Ganguly et al. | 536/17 |
| 4,279,896 | 7/1981 | Ganguly et al. | 424/180 |
| 4,579,940 | 4/1986 | Fujiwara et al. | 536/7.1 |
| 4,920,103 | 4/1990 | Kirst et al. | 514/30 |
| 4,921,947 | 5/1990 | Tao et al. | 536/7.1 |
| 5,032,581 | 7/1991 | Lukacs et al. | 514/30 |
| 5,043,324 | 8/1991 | Lukacs et al. | 514/30 |
| 5,140,014 | 8/1992 | Maring et al. | 514/30 |

FOREIGN PATENT DOCUMENTS 2135670  9/1984  United Kingdom .
9402496  2/1994  WIPO .

OTHER PUBLICATIONS

B. S. Bal et al., Tetrahedron, vol. 37, pp. 2091–2096, 1981.
K. Funaishi et al., J. of Antibiotics, pp. 938–947, vol. XLIII No. 8, 1990.
H. Koshiyama et al., J. of Antibiotics, pp. 61–64, vol. XXII No. 2, 1969.
H. Kirst et al., J. of Antibiotics, pp. 1673–1683, vol. XXXV No. 12, 1982.
H. Kirst et al., J. of Antibiotics, pp. 823–842, vol. XL No. 6, 1987.
Wagman et al., J. of Antibiotics, pp. 641–646, vol. XXV No. 11, 1972.

*Primary Examiner*—Elli Peselev
*Attorney, Agent, or Firm*—Peter C. Richardson; Gregg C. Benson

[57] ABSTRACT

Derivatives of 16-membered ring 3-deoxy macrolide antibiotic derivatives of rosaramicin, repromicin, 5-mycaminosyltylonolide, desmycosin, lactenocin, O-demethyllactenocin, cirramycin $A_1$, and 23-deoxymycaminosyltylonolide, which are useful against bacterial and mycoplasmic pathogens in animals.

15 Claims, No Drawings

ANTIBIOTIC MACROLIDES

CROSS REFERENCE TO RELATED APPLICATION

This application is a nonprovisional application claiming benefit of provisional application Ser. No. 60/008,196, filed Dec. 5, 1995.

BACKGROUND OF THE INVENTION

This invention is concerned with new antibiotics. In particular, this invention relates to compounds which are derivatives of the 3-deoxy macrolide antibiotics which have been derived from rosaramicin, repromicin, 5-mycaminosyltylonolide, desmycosin, lactenocin, O-demethyllactenocin, cirramycin $A_1$, and 23-deoxymycaminosyltylonolide; to the pharmaceutically-acceptable acid addition salts of such derivatives; to methods of using such derivatives in the treatment of illnesses in animals caused by bacterial and mycoplasmic pathogens; and to pharmaceutical compositions useful therefor. The term "animals" includes mammals, fish and birds.

There are numerous agents known to combat bacterial infectious diseases in animals, but for many specific diseases the current agents of choice leave much to be desired. In some instances the agents may not persist long enough in the host and, therefore, require frequent dosing to maintain therapeutically effective blood and/or tissue levels. For meat producing animals (e.g., cattle, poultry, sheep and swine) this will require considerable labor intensive animal handling which is costly to the producer. In other cases, the agent may be poorly tolerated or even toxic to the host at therapeutically effective doses. Agents with increased potency, a longer half-life, an increased therapeutic index and a broader spectrum of antibacterial activity as well as—agents with greater oral absorption would improve the scope of animal diseases that could be more effectively treated. Thus, the need for new antibacterial and antimycoplasmic agents with improved properties endures.

Diseases of particular concern are: bovine respiratory disease, the principal causative bacterial pathogens of which are *Pasteurella haemolytica*, *P. multocida* and *Haemophilus somnus;* pasteurellosis in swine, goats, sheep and poultry I.P. multocida); swine pleuropneumonia (*Actinobacillus pleuropneumoniae*); swine streptococcus infections (*Streptococcus suis*); and for all of the above mentioned hosts, infections by *Mycoplasma spp.*

Derivatives of tylosin and its related macrolides have been shown to be effective against infections in poultry, cattle and swine caused by certain gram-positive and gram-negative bacteria: Kirst et al., U.S. Pat. Nos. 4,920,103; Tao et al., 4,921,947; Kirst et al., U.K. Patent Application GB 2135670A.

Other antibiotic macrolides have been claimed in co-pending U.S. applications, application Ser. No. 08/362,496 filed Jan. 11, 1995 (published in WO 94/02496) and application Ser. No. 08/311,285 filed Sep. 22, 1994, and in co-pending PCT applications, application Ser. No. PCT/US94/00095 filed Jan. 6, 1994 published in WO 94/21657 and application Ser. No. PCT/IB94/00199 filed Jul. 4, 1994 published in WO 95102594, all of which are assigned to the assignee hereof.

SUMMARY OF THE INVENTION

This invention is concerned with new antibiotics which are derivatives of 3-deoxy macrolide antibiotics which have been derived from repromicin, rosaramicin, 5-mycaminosyltylonolide, desmycosin, lactenocin, O-demethyllactenocin, cirramycin $A_1$, and 23-deoxymycaminosyltylonolide and to the acid addition salts of such derivatives. These new antibiotics have enhanced potency against bacterial pathogens over the parent compounds and are active against mycoplasmic pathogens.

The compounds of the present invention are of the formula (I) or (II)

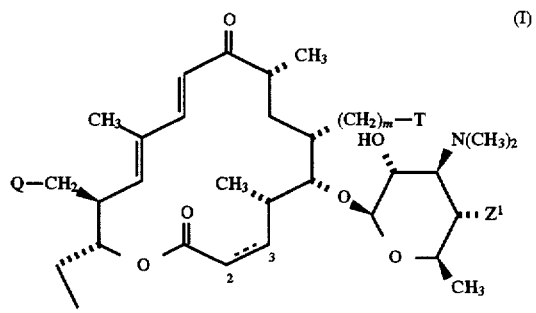

or

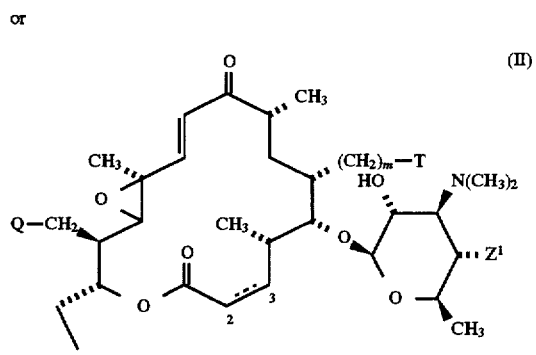

or the pharmaceutically acceptable salts thereof, wherein m is 1 or 2;

$Z^1$ is H, OH or mycarosyloxy;

represents a single or a double bond wherein the double bond results in either the cis or trans geometry;

Q is selected from the group consisting of H, OH, fluoro, chloro, bromo, iodo, $OX^1$,

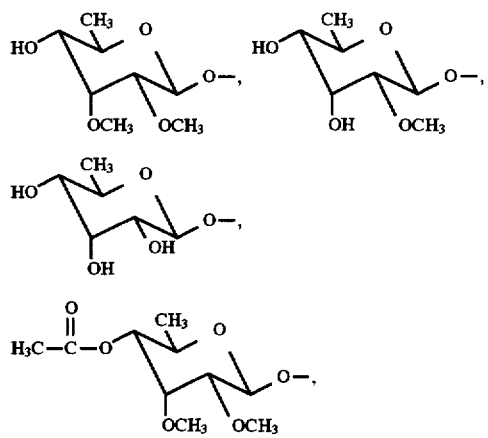

azetidin-1-yl, pyrrolidin-1-yl, piperidin-1-yl, 3,3-dimethylpiperidin-1-yl, hexahydroazepin-1-yl, octahydroazocin-1-yl, octahydroindol-1-yl, 1,3,3a,4,7,7a-hexahydroisoindol-2-yl, decahydroquinol-1-yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholino, 2,6-dimethylmorpholin-4-yl, thiomorpholino, and —$NX^2X^3$;

$X^1$ is selected from the group consisting of optionally substituted alkyl having 1 to 4 carbons, optionally substituted cycloalkyl having 4 to 8 carbon atoms, and an optionally substituted aryl, aralkyl or heteroaryl group selected from the group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl;

where the optionally substituted aryl, aralkyl and heteroaryl groups are optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion;

$X^2$ and $X^3$ are each independently selected from the group consisting of hydrogen, alkyl having 1 to 4 carbons, hydroxyalkyl having 2 to 4 carbons, cycloalkyl having 3 to 8 carbons, alkenyl having 3 or 4 carbons, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion;

T is
—$C(=O)(Z^3)$, —$CH_2$—$N(B)(CH_2)_a$—$C(=O)(Z^3)$, —$CH_2$—$N(Z^2)(C=O)$—$(CH_2)_a$—$Z^3$, —$CH_2$—$N(B)(CH_2)_g$—$N(B)(CH_2)_a$—$C(=O)(Z^3)$, —$CH=CH$—$(CH_2)_n$—$(Z^4)$ $(Z^5)$, —$CH(Z^8)N(Z^5)(Z^6)(Z^7)$,

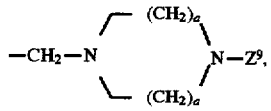

—$CH_2$—$N(Z^{12})(SO_2Z^{13})$, —$CH_2$—$N(Z^{12})(C(=O)$—$Z^{14}$—$Z^{13})$, —$CH_2$—$N(Z^{12})(CH_2)_g$—$N(Z^{15})(C(=O)$—$Z^{14}$—$Z^{13})$ or —$CH_2$—$N(Z^{12})(CH_2)_g$—$N(Z^{15})(SO_2$—$Z^{13})$;

wherein n is an integer from 1 to 4;

B for each occurrence is independently selected from the group consisting of hydrogen, ($C_1$–$C_4$)alkyl, an aminoacyl group and a dipeptidyl group;

$Z^2$ is hydrogen or ($C_1$–$C_4$)alkyl;

$Z^3$ is —$N(R^1R^2)$, —$NH$—$CH(R^3)$—$(CH_2)_e$—$COOR^4$ or —$NH$—$CH(R^3)$—$(CH_2)_e$—$C(=O)$—$NH$—$(CH_2)_f$—$COOR^4$;

$R^1$ and $R^2$ are each independently selected from the group consisting of hydrogen, methyl, optionally substituted alkyl having 2 to 6 carbons, optionally substituted cycloalkyl having 3 to 8 carbons, aminoalkyl having 2 to 6 carbons, hydroxyalkyl having 2 to 6 carbons, N-alkylamino-alkyl having 1 to 4 carbons in the alkylamino portion and 2 to 4 carbons in the alkyl portion, optionally substituted benzyl, optionally substituted phenyl, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion, —$(CH_2)_g$-morpholino, —$(CH_2)_g$-piperidino, —$(CH_2)_g$-pyrrolidino, —$(CH_2)_g$-azetidin-1-yl, and —$(CH_2)_g$-hexahydroazepin-1-yl;

or $R^1$ and $R^2$ are taken together with the nitrogen to which they are attached and form $Z^{100}$;

$R^3$ corresponds to just the side chain portion of amino acids and for each occurrence is independently selected from the side chain of the group of amino acids consisting of the D- or L-form, when applicable, of alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, tryptophan, tyrosine, valine, β-alanine, β-lysine, α,α-dimethylglycine, α-aminobutyric acid, 4-hydroxyphenylglycine, phenylglycine, α,γ-diaminobutyric acid, ornithine and homoserine;

e is 0 or 1, provided that when e is 1 then $R^3$ corresponds to the side chain of β-lysine or β-alanine;

f is 0 or 1, provided that when f is 1 then $R^3$ corresponds to the side chain of β-lysine or β-alanine;

$R^4$ is H, alkyl having 1 to 4 carbons or benzyl;

$Z^4$ is selected from the group consisting of hydrogen, an aminoacyl group, a dipeptidyl group, alkenyl having 3 to 5 carbons provided that the double bond is not adjacent to the nitrogen to which $Z^4$ is attached, alkynyl having 3 to 5 carbons provided that the triple bond is not adjacent to the nitrogen to which $Z^4$ is attached, hydroxyalkyl having 2 to 4 carbons in the alkyl portion, $Q^{10}$, $Q^{20}$, $Q^{30}$, and alkoxyalkyl having 2 to 4 carbons in the alkyl portion and 1 to 4 carbons in the alkoxy portion;

$Z^5$ is selected from the group consisting of hydrogen, alkenyl having 3 to 5 carbons provided that the double bond is not adjacent to the nitrogen to which $Z^5$ is attached, alkynyl having 3 to 5 carbons provided that the triple bond is not adjacent to the nitrogen to which $Z^5$ is attached, hydroxyalkyl having 2 to 4 carbons in the alkyl portion, $Q^{10}$, $Q^{20}$, $Q^{30}$, alkoxyalkyl having 2 to 4 carbons in the alkyl portion and 1 to 4 carbons in the alkoxy portion and —$R^6$—$N(R^7R^8)$;

$Q^{10}$ for each occurrence is independently

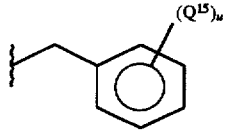

where u is an integer from 1 to 5 and $Q^{15}$ for each occurrence is independently selected from the group consisting of ($C_1$–$C_4$)alkyl, ($C_1$–$C_4$)alkoxy, fluoro, chloro, bromo, iodo, nitro, amino, cyano, hydroxy, trifluoromethyl and carboalkoxy having 1 to 4 carbons;

$Q^{20}$ for each occurrence is independently an optionally substituted ($C_1$–$C_4$)alkyl, optionally substituted with a substituent selected from the group consisting of hydroxy, cyano, N-alkylamino having 1 to 5 carbons and N,N-dialkylamino having a total of 2 to 6 carbons;

$Q^{30}$ for each occurrence is independently

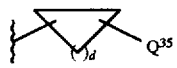

where d is an integer from 1 to 5 and $Q^{35}$ is selected from the group consisting of hydroxy, cyano, N-alkylamino having 1 to 5 carbons and N,N-dialkylamino having a total of 2 to 6 carbons;

$R^6$ is $(C_2-C_4)$alkylene;

$R^7$ is selected from the group consisting of hydrogen, alkyl having 1 to 4 carbons, cycloalkyl having 3 to 8 carbons and alkoxyalkyl having 2 to 4 carbons in the alkyl portion and 1 to 4 carbons in the alkoxy portion;

$R^8$ is selected from the group consisting of alkyl having 1 to 4 carbons, an optionally substituted hydroxyalkanoyl having 1 to 6 carbons, an aminoacyl group and a dipeptidyl group, wherein the optionally substituted hydroxyalkanoyl group is optionally substituted with an optionally substituted phenyl group;

or $R^7$ and $R^8$ are taken together with the nitrogen to which they are attached and form a cyclic amine having 3 to 6 carbon atoms;

or $Z^4$ and $Z^5$ are taken together with the nitrogen to which they are attached and form $Z^{100}$;

$Z^6$ is an aminoacyl group, a dipeptidyl group or is independently selected from the same group as defined for $R^1$;

$Z^7$ is independently selected from the same group as defined for $R^1$ or from the group consisting of

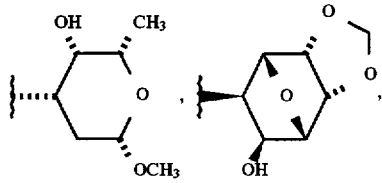

$-[(CH_2)_g-R^{12}]_q-(CH_2)_g-N(Z^{16})_2$ and $-R^9-N(R^{10}R^{11})$;

wherein q is 1, 2 or 3;

$R^9$ is $(C_2-C_4)$alkylene optionally substituted with $(C_{1-4})$alkyl or hydroxy provided that the hydroxy can only be attached to the C2 of the alkylene group when the alkylene is three carbon atoms long or to the C3 of the alkylene group when the alkylene is four carbon atoms long;

$R^{10}$ is selected from the group consisting of hydrogen, methyl and ethyl;

$R^{11}$ is selected from the group consisting of an optionally substituted hydroxyalkanoyl having 1 to 6 carbons, an amino acyl group, and dipeptidyl group, the optionally substituted hydroxyalkanoyl group is optionally substituted with an optionally substituted phenyl;

or $R^{10}$ and $R^{11}$ are taken together with the nitrogen to which they are attached and form $Z^{100}$;

$R^{12}$ is S or O;

$Z^{16}$ for each occurrence is independently selected from the group consisting of an aminoacyl group, dipeptidyl group and the same group of substituents as is defined hereinbelow for $Z^{12}$, $Z^{13}$ and $Z^{15}$;

or $Z^6$ and $Z^7$ are taken together with the nitrogen to which they are attached and form $Z^{100}$;

$Z^8$ is H or CN;

$Z^9$ is $(C_{1-6})$alkyl, amino acyl group, dipeptidyl group, hydroxyalkanoyl having 1 to 6 carbons, aminoalkyl having 2 to 6 carbons, hydroxyalkyl having 2 to 4 carbons, N-alkylaminoalkyl having 1 to 4 carbons in the alkylamino portion and 2 to 4 carbons in the alkyl portion, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion, $-CO-Z^{14}-Z^{13}$ or $-SO_2-Z^{13}$;

$Z^{12}$, $Z^{13}$ and $Z^{15}$ for each occurrence are each independently selected from the same group as defined for $R^1$, provided that $Z^{13}$ is hydrogen only when $Z^{14}$ is NH;

$Z^{14}$ for each occurrence is independently O or NH;

a for each occurrence is independently 1 or 2;

for each occurrence of the amino acyl group and dipeptidyl group, the amino acyl group and the amino acyl groups of the dipeptidyl group are independently selected from the group consisting of the D- or L-form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, iysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

for each occurrence of an optionally substituted alkyl or optionally substituted cycloalkyl, the optionally substituted alkyl or optionally substituted cycloalkyl is independently selected from an optionally substituted alkyl or optionally substituted cycloalkyl optionally substituted with 1, 2 or 3 substituents independently selected from the group consisting of hydroxy, cyano, fluoro, trifluoromethyl, optionally substituted amino, optionally substituted N-alkylamino having 1 to 4 carbons, N,N-dialkylamino having a total of 2 to 6 carbons, N—(hydroxyalkyl)amino having 2 to 4 carbons, N,N-bis(hydroxyalkyl)amino wherein each alkyl portion has 2 to 4 carbons, alkoxy having 1 to 4 carbons, alkoxycarbonyl having 1 to 4 carbons in the alkoxy portion, N,N-dialkylaminoalkoxy having a total of 2 to 6 carbons in the dialkylamino portion and 2 to 4 carbons in the alkoxy portion, alkoxyalkoxy having 1 to 4 carbons in each of the alkoxy portions, alkoxyalkoxyalkoxy having 1 to 4 carbons in each of the alkoxy portions, spirocycloalkyl having 4 to 6 carbons,

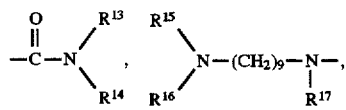

-continued

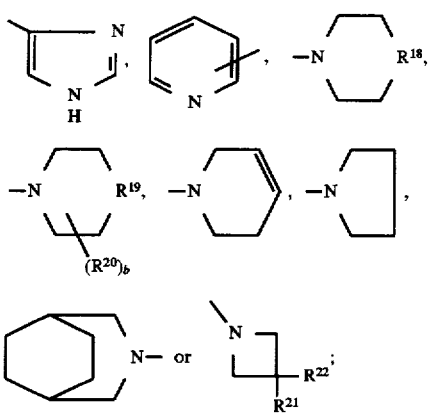

wherein the optionally substituted amino and the optionally substituted N-alkylamino are each independently optionally mono-substituted with an aminoacyl group or a dipeptidyl group;

$R^{13}$ and $R^{14}$ are each independently selected from the group consisting of hydrogen and alkyl having 1 to 4 carbons;

or $R^{13}$ and $R^{14}$ are taken together with the nitrogen to which they are attached and form $Z^{100}$;

$R^{15}$, $R^{16}$, and $R^{17}$ are each independently selected from the group consisting of hydrogen, $(C_1-C_4)$alkyl, an aminoacyl group and a dipeptidyl group;

$R^{18}$ is NH, S, N-$(C_1-C_4)$alkyl, N—(amino acyl group), or N-(dipeptidyl group);

$R^{19}$ is selected from the group consisting of C, CH, $CH_2$, N and NH;

$R^{20}$ is alkyl having 1 to 4 carbons or —$COOR^{21}$;

$R^{21}$ for each occurrence is independently H or alkyl having 1 to 4 carbons;

$R^{22}$ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or $R^{21}$ and $R^{22}$ are taken together and form an oxo group;

$Z^{100}$ for each occurrence is independently selected from the group consisting of

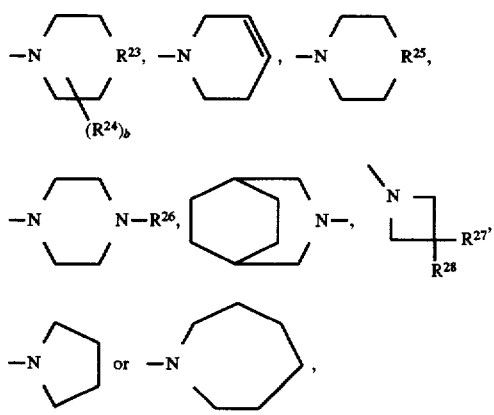

where
$R^{23}$ is selected from the group consisting of C, CH, $CH_2$, N, NH, N(amino acyl) or N(dipeptidyl group);

$R^{24}$ is alkyl having 1 to 4 carbons, —CO—$(C_1-C_4)$alkyl or —COO—$(C_1-C_4)$alkyl;

$R^{25}$ is O or S;

$R^{26}$ is selected from the group consisting of alkyl having 1 to 4 carbons, an optionally substituted hydroxyalkanoyl having 1 to 6 carbons, an amino acyl group and a dipeptidyl group,
wherein the optionally substituted hydroxyalkanoyl group is optionally substituted with an optionally substituted phenyl group;

$R^{27}$ is H or alkyl having 1 to 4 carbons;

$R^{28}$ is H, alkyl having 1 to 4 carbons, hydroxy, alkoxy having 1 to 3 carbons, amino, N-alkylamino having 1 to 4 carbons or N,N-dialkylamino having a total of 2 to 6 carbons;

or $R^{27}$ and $R^{28}$ are taken together and form an oxo;

g for each occurrence is independently 2, 3, or 4;

b for each occurrence is independently 0, 1 or 2; and for each occurrence of the optionally substituted phenyl or optionally substituted benzyl, the optionally substituted phenyl or optionally substituted benzyl is optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, —NH—CO—$CH_3$, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion; with the following provisos:

(1) that when T is —C(=O)($Z_3$), —$CH_2$—N(B)($CH_2$)$_a$—C(=O)($Z^3$), —$CH_2$—N($Z^2$)(C=O)—$(CH_2)_a$—$Z^3$ or —$CH_2$—N(B)$(CH_2)_9$—N(B)$(CH_2)_a$—C(=O)($Z^3$) wherein $Z^3$ is —N($R^1R^2$) where $R^1$ or $R^2$ is a substituted alkyl or substituted cycloalkyl, then the substituent at the 1-position of the substituted alkyl or substituted cycloalkyl cannot be fluoro, chloro or a heteroatom attached substituent; and (2) when any of the substituents defined above which may be a substituted cycloalkyl is a substituted cycloalkyl, then the substituent at the 1-position of the substituted cycloalkyl cannot be fluoro, chloro or a heteroatom attached substituent.

The term "loweralkyl" denotes an alkyl having 1 to 4 carbons. The term "alkyl" is meant to encompass both straight chain and branched alkyls.

Those skilled in the art will recognize that some of the compounds of the present invention possess stereochemical centers. In those cases where stereo-chemical centers are present it is understood that all of the stereoisomers are within the scope of this invention. Further, in those cases where the bond between the C2 and C3 of the macrolide is a double bond both the cis and trans form are within the scope of this application.

The amino acyl groups are derivatives of the corresponding amino acids and are well known in the art. The following D- or L-amino acids, where applicable, are used to derive the amino acyl groups of this invention: alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, tryptophan, tyrosine, valine, β-alanine, β-lysine, N,N-dimethylglycine, α,α-dimethylglycine, α-aminobutyric acid, 4-hydroxyphenylglycine, phenylglycine, α,α-diaminobutyric acid, ornithine, homoserine, bicine, N,N-diethyl-β-alanine, N,N-dimethyl-γ-aminobutyric acid, and sarcosine.

The dipeptidyl groups comprise derivatives of any possible combination of two of the amino acids listed hereinabove which can be coupled by conventional peptide synthesis methods well known to those skilled in the art.

A group of preferred compounds are those compounds having the formula (I) or the pharmaceutically acceptable salts thereof wherein m is 1 and $Z^1$ is H or OH.

A group of more preferred compounds are those compounds having the formula (I) or a pharmaceutically acceptable salt thereof wherein m is 1; $Z^1$ is H or OH; T is —$CH_2$—$N(B)(CH_2)_a$—$C(=O)(Z^3)$, —$CH_2$—$N(Z^2)$ ($C=O$)—$(CH_2)_a$—$Z^3$, —$CH_2$—$N(B)(CH_2)_g$—$N(B)(CH_2)_a$—$C(=O)(Z^3)$, —$CH=CH$—$(CH_2)_n$—$N(Z^4)(Z^5)$, —$CH(Z^8)N(Z^6)(Z^7)$,

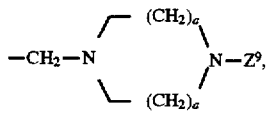

—$CH_2$—$N(Z^{12})(SO_2Z^{13})$, —$CH_2$—$N(Z^{12})(C(=O)$—$Z^{14}$—$Z^{13})$, —$CH_2$—$N(Z^{12})(CH_2)_g$—$N(Z^{16})(C(=O)$—$Z^{14}$—$Z^{13})$ or —$CH_2$%13 $N(Z^{12})(CH_2)_g$—$N(Z^{15})(SO_2Z^{13})$ where a, g, n, Q, $Z^2$, $Z^3$, $Z^4$, $Z^5$, $Z^6$, $Z^7$, $Z^8$, $Z^9$, $Z^{12}$, $Z^{13}$, $Z^{14}$ and $Z^{15}$ are as defined hereinabove.

A group of an even more preferred group of compounds are those compounds having the formula (I) or a pharmaceutically acceptable salt thereof wherein m is 1; $Z^1$ is H or OH; T is —$CH=CH$—$(CH_2)_n$—$N(Z^4)(Z^5)$, —$CH(Z^8)N(Z^6)(Z^7)$,

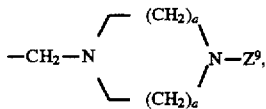

—$CH_2$—$N(Z^{12})(SO_2Z^{13})$, —$CH_2$—$N(Z^{12})(C(=O)$—$Z^{14}$—$Z^{13})$, —$CH_2$—$N(Z^{12})(CH)_g$—$N(Z^{15})(C(=O)$—$Z^{14}$—$Z^{13})$ or —$CH_2$—$N(Z^{12})(CH_2)_g$—$N(Z^{15})(SO_2$—$Z^{13})$ where a, g, n, Q, $Z^4$, $Z^5$, $Z^6$, $Z^7$, $Z^9$, $Z^{12}$, $Z^{13}$, $Z^{14}$ and $Z^{15}$ are as defined hereinabove and $Z^8$ is H.

Yet a group of even more preferred compounds are those compounds having the formula (I) or a pharmaceutically acceptable salt thereof of formula (I) wherein m is 1; $Z^1$ is H or OH; T is —$CH=CH$—$(CH_2)_n$—$N(Z^4)(Z^5)$, —$CH_2$—$N(Z^6)(Z^7)$ or

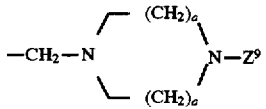

where n is 1; $Z^4$ and $Z^5$ are each independently selected from the group consisting of hydrogen, alkenyl having 3 to 5 carbon atoms provided that the double bond is not adjacent to the nitrogen to which the alkenyl is attached, alkynyl having 3 to 5 carbons provided that the triple bond is not adjacent to the nitrogen to which the alkynyl is attached, hydroxyalkyl having 2 to 4 carbons in the alkyl portion, $Q^{10}$, $Q^{20}$, $Q^{30}$ and alkoxyalkyl having 2 to 4 carbons in the alkyl portion and 1 to 4 carbons in the alkoxy portion, or $Z^4$ and $Z^5$ are taken together with the nitrogen to which they are attached and form $Z^{100}$; and a, Q, $Z^6$, $Z^7$, $Z^9$, $Q^{10}$, $Q^{20}$, $Q^{30}$, $Z^{100}$ are as defined hereinabove for the formulae (I) and (II).

A group of especially more preferred compounds are those compounds having the formula (I) or a pharmaceutically acceptable salt thereof wherein m is 1; $Z^1$ is H or OH; T is —$CH_2$—$N(Z^6)(Z^7)$ or

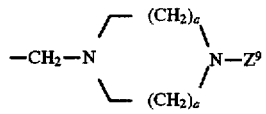

where $Z^6$ is independently selected from the same group of substituents as $R^1$; $Z^7$ is independently selected from the same group of substituents as $R^1$ or is —$R^9$—$N(R^{10}R^{11})$; or $Z^6$ and $Z^7$ are taken together with the nitrogen to which they are attached and form $Z^{100}$; and $Z^9$ is amino acyl group, aminoalkyl having 2 to 6 carbons, hydroxyalkyl having 2 to 4 carbons, N-alkylaminoalkyl having 1 to 4 carbons in the alkylamino portion and 2 to 4 carbons in the alkyl portion, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion or —$CO$—$Z^{14}$—$Z^{13}$; and a, Q, $R^1$, $R^9$, $R^{10}$, $R^{11}$, $Z^{13}$, $Z^{14}$, $Z^{100}$ are as defined hereinabove for formulae (I) and (II).

A first group of most preferred compounds are those compounds having the formula (I) or a pharmaceutically acceptable salt thereof wherein m is 1; Q is OH; $Z^1$ is H; and T is —$CH_2$—$N(Z^6)(Z^7)$ where $Z^6$ is hydrogen, methyl or optionally substituted alkyl having 2 to 6 carbon atoms; $Z^7$ is N-alkylaminoalkyl having 1 to 4 carbons in the alkylamino portion and 2 to 4 carbons in the alkyl portion, optionally substituted alkyl having 2 to 6 carbon atoms or optionally substituted cycloalkyl having 3 to 8 carbons; or $Z^6$ and $Z^7$ are taken together with the nitrogen to which they are attached and form pyrrolidino, piperidino 3,4-dehydropiperidino or azabicyclononan-3-yl. Especially preferred within the foregoing first group of most preferred compounds are those compounds or a pharmaceutically acceptable salt thereof wherein said optionally substituted alkyl of $Z^6$ is propyl; said optionally substituted alkyl of $Z^7$ is propyl, 3-(dimethylamino)-propyl or 2-spirocyclo-pentyl-3-hydroxypropyl; and said optionally substituted cycloalkyl of $Z^7$ is cyclohexyl.

A second group of most preferred compounds are those compounds having the formula (I) or a pharmaceutically acceptable salt thereof wherein m is 1; Q is OH; $Z^1$ is H; and T is —$CH_2$—$N(Z^6)(Z^7)$ where $Z^6$ hydrogen or methyl; $Z^7$ is methyl, 2-fluoroethyl, 2,2-dimethyl-3-hydroxypropyl, 2-hydroxyethyl, propyl, 3-hydroxypropyl, 2,5-(dihydroxy)-cyclohexyl or 3-aminopropyl; or $Z^6$ and $Z^7$ are taken together with the nitrogen to which they are attached and form 4-methylpiperazino, azetidino, 4-hydroxypiperidino, morpholino or 3-hydroxypiperidino.

A third group of most preferred compounds are those compounds having the formula (I) or a pharmaceutically acceptable salt thereof wherein m is 1; Q is OH; $Z^1$ is OH; and T is —$CH_2$—$N(Z^6)(Z^7)$ where $Z^6$ is hydrogen; $Z^7$ is 2,2-dimethyl-3-hydroxypropyl; or $Z^6$ and $Z^7$ are taken together with the nitrogen to which they are attached and form hexahydroazepin-1-yl.

A fourth group of most preferred compounds are those compounds having the formula (I) or a pharmaceutically acceptable salt thereof wherein m is 1; the bond between C2–C3 of the macrolide is a double bond, Q is OH; $Z^1$ is OH; and T is —$CH_2$—$N(Z^6)(Z^7)$ where $Z^6$ is hydrogen, methyl or propyl; $Z^7$ is 2,2-dimethyl-3-hydroxypropyl, methyl, propyl or 3-(dimethylamino)propyl; or $Z^6$ and $Z^7$ are taken together with the nitrogen to which they are attached and form hexahydroazepin-1-yl or 3-azabicyclononan-3-yl.

Thus, in a further aspect, the invention provides pharmaceutical compositions comprising a compound of the formula (I) or (II), or a pharmaceutically acceptable salt thereof, and a pharmaceutically acceptable carrier or diluent.

This invention also provides methods of treating a bacterial infection or a mycoplasmic infection in an animal in need thereof, which methods comprise administering to said animal a bacterial or mycoplasmic treating amount of a compound of the formula (I) or (II), or a pharmaceutically acceptable salt thereof.

This invention further provides a method of using the compounds of claim 1 or the pharmaceutically acceptable salts thereof prophylactically in treating animals susceptible to a bacterial or mycoplasmic infection.

DETAILED DESCRIPTION OF THE INVENTION

The compounds of the present invention, having the formula (I) or (II), as defined above, are readily and generally prepared by reductive amination reactions of the appropriate 3-deoxy macrolide derivatives of rosaramicin, repromicin, 5-mycaminosyl-tylonolide, desmycosin, lactenocin, O-demethyllactenosin, cirramycin $A_1$, or 23-deoxy-mycaminosyltylonolide, with an amine, optionally followed by conversion to the acid addition salt as shown in the methods of the Examples hereinbelow, in methods analogous thereto and by the methods described immediately below.

Repromicin was prepared according to the following fermentation procedure.

Fermentor scale:

To prepare frozen lots for use as standard inoculum, *Micromonospora rosaria*, ATCC 55709, deposited Sep. 5, 1995, is inoculated into JDYTT medium (cerelose 10 g/L, corn starch 5 g/L, corn steep solids 2.5 g/L, NZ Amine YTT 5 g/L, $COCl_2.6H_2O$ 0.002 g/L, P-2000 (polyglycol, available from George Mann & Co., Inc., 175 Terminal Road, Providence, R.I.) 1 ml/L, $CaCO_3$ 3 g/L) and shaken (250 rpm, 30° C., 2 inch throw) for about three days. The JDYTT medium, adjusted to about pH 7.0, was sterilized at about 121° C. for about 30 minutes prior to use. Glycerol (final concentration 20%) is added as a cryoprotectant, and the culture is stored at about −80° C. To prepare the inoculum, 5 ml of the frozen culture lot is transferred to 1 liter of JDYTT medium in a 2.8 L fernbach flask. The culture is grown for about 3 days at about 30° C. with shaking (250 rpm, 2 inch throw). The entire contents of the fernbach are transferred to 8 L of production medium RSM-6 in a 14 L fermentor jar (New Brunswick Scientific, New Brunswick, N.J.) with two 4¾ inch agitator blades. The composition of RSM-6 is corn starch 50 g/L, cerelose 10 g/L, ardamine PH 5 g/L (available from Champlain Industries Inc., 79 State Street, Harbor Beach, Mich.), Pharmamedia 8–10 g/L (available from The Buckeye Cellulose Corporation, P.O. Box 8407, Memphis, Tenn.), $MgHPO_4.3H_2O$ 10 g/L, casein hydrolysate 2.5 g/L (available from Sheffield Chemical, Norwich, N.Y.), asparagine 0.5 g/L, $FeSO_4.7H_2O$ 0.028 g/L, $MgSO_4.7H_2O$ 0.5 g/L, $K_2HPO_4$ 0.75 g/L, $CuSO_4.5H_2O$ 0.003 g/L, $MnCl_2.4H_2O$ 0.003 g/L, $ZnSO_4.7H_2O$ 0.003 g/L, $COCl_2.6H_2O$ 0.003 g/L, P2000 1 ml/L. RSM-6 is adjusted to about pH 7.0 and autoclaved for about 99 minutes at about 121° C. prior to use. The fermentation is run at about 30° C., 450 rpm, 0.34 v/vim air, with pH controlled between 6.7 and 7.3 with $NaOH/H_2SO_4$ or by addition of 6 g/L MOPS to production medium. Repromicin titers typically peak between 69 and 116 hours. Samples are extracted into a solvent mixture (3.5:6.5 methanol:0.1M $KH_2PO_4$ buffer, pH 3.5).

Flask scale:

Inoculum is prepared as described above or by adding 2 ml of frozen culture lot to 30 ml JDYTT inoculum medium in a 300 ml Erlenmeyer flask. The culture is grown for about 3 days at about 30° C. with shaking (250 rpm, 2 inch throw). Two ml of inoculum are transferred into about 30 ml modified RSM-5 medium (corn starch 30 g/L, 10 g/L pharmamedia, 10 g/L cerelose, 5.0 g/L ardamine PH, 0.5 g/L asparagine, $FeSO_4.7H_2O$ 0.028 g/L, $MgSO_4.7H_2O$ 0.5 g/L, $K_2HPO_4$ 0.75 g/L, $CUSO_4.5H_2O$ 0.002 g/L, $MnCl_2.4H_2O$ 0.003 g/L, $ZnSO_4.7H_2O$ 0.003 g/L, MOPS 6 g/L, casein hydrolysate 2.5 g/L and $MgHPO_4.3H_2O$ 10 g/L, P-2000 1 ml/L, pH 7.0, and are autoclaved at about 121° C. for about 20 minutes) in a 300 ml Erlenmeyer flask. The flasks are shaken for 3–4 days at about 30° C. Fermentation broth is extracted as described above.

Derivatization of the parent macrolide at the C-23 position is carried out according to a method analogous to the method well known to those of ordinary skill in the art and as described in J. Antibiotics, 40(6), pp. 823–842, 1987, the contents of which are incorporated herein by reference.

5-OMT was obtained according to the method set out in R. B. Morin and M. Gorman, Tet. Let., 2339 (1964). The starting macrolide rosaramicin is produced and isolated according to the method described by Wagman et al. in Journal of Antibiotics, Vol. XXV, No. 11, pp. 641–646, November 1972. Desmycosin, lactenocin, O-demethyllactenocin and 23-deoxymycaminosyltylonolide are produced and isolated according to the method described in Journal of Antibiotics, 35(12), pp. 1675–1682, 1982. Cirramycin $A_1$, is produced and isolated according to the method described in Journal of Antibiotics, 22, p. 61, 1969. The contents of the above references are incorporated herein by reference. All other starting materials and reagents required for the synthesis of the compounds of the present invention are readily available commercially or can be prepared according to methods known in the art.

Compounds of the present invention of formula (I) or (II) where m is 2 can be prepared by application of Wittig chemistry using the ylide prepared from (methoxymethyl) triphenylphosphonium chloride. Typically, the phosphonium salt is suspended in an aprotic solvent such as THF, diethyl ether, or dioxane. To this mixture is added a base, such as potassium t-butoxide, n-butyllithium, or sodium hydride, usually at about −20° to 30° C., and the solution is then stirred for about 10 to 120 minutes. A solution of the 3-deoxy macrolide is then added and the resulting solution is stirred for 1 to 24 hours at room temperature. After a standard extractive work-up, the crude product is dissolved in a solvent such as THF or dioxane, and aqueous acid, e.g. 1N HCl, is added. Stirring for 2 to 12 hours and extractive work-up produces a macrolide aldehyde that can be used for other reactions described herein.

This invention relates to compounds which are derivatives of 3-deoxy macrolide antibiotics. Several methods are known to those skilled in the art for converting 3-hydroxy macrolides to the 3-deoxy analogs. Usually the C3 alcohol of a suitably protected macrolide is derivatized as a sulfonate or an acetate, preferably as the mesylate. This is typically done with methanesulfonyl chloride in pyridine. The activated group is then eliminated, usually by treatment with a base such as potassium carbonate or an amine. The preferred method is to use ammonium hydroxide in methanol. In certain cases, the resulting double bond is reduced, usually by hydrogenation with a metal catalyst such as Raney nickel.

Some of the compounds described in this invention require the formation of ureas and sulfonamides from a starting amine. Ureas are formed using standard conditions, such as reaction of the amine in an inert solvent (e.g., toluene or $CH_2Cl_2$) with an isocyanate. An external base such as triethylamine may be used. Some isocyanates are commercially available or can be prepared by the reaction of a primary amine with phosgene or an equivalent (e.g., triphosgene). Other methods for isocyanate formation are suitable as well, such as Hofmann, Curtius, Lossen, and Schmidt rearrangements from carboxylic acid derivatives. Sulfonamides are most readily formed by reaction of an amine with a sulfonyl chloride, usually done in an inert solvent such as DMF with a base such as sodium carbonate.

The following procedure is used for a Wittig reaction when T is $—CH=CH—(CH_2)_n—N(Z^4)(Z^5)$. To a solution of excess phosphonium bromide (usually 3-fold excess over the macrolide), prepared as described below, in a reaction inert solvent such as toluene, is added an equimolar amount of base, such as potassium bis(trimethylsilyl)amide, 0.5M in toluene. The reaction mixture is stirred for about 5 to 90 minutes, usually for about 15 minutes, at about 5° to 35° C., usually at ambient temperature. To the yellow-orange mixture is added solid 3-deoxy macrolide aldehyde, followed by stirring at about 0° to 80° C., usually at ambient temperature. After having been stirred for about 30 minutes to 24 hours, preferably about one hour, the desired olefin product is isolated by standard techniques well known to those skilled in the art, such as silica gel chromatography or recrystallization.

The phosphonium bromide reagents used for the above Wittig reactions can be prepared by a number of methods. (2-Aminoethyl)triphenyl-phosphonium bromides generally are synthesized by reacting a secondary amine with vinyltriphenylphosphonium bromide, usually without additional solvents, and stirring the mixture at about 25° to 150° C., usually at about 80° C., for 0.5 to 3 days, usually for one day. (Procedure modified from J. Org. Chem. 29, pp. 1746–1751, 1964). At this time, the reaction mixture is mixed with an aprotic solvent, preferably diethyl ether, and the solids collected by filtration and rinsed well with the same solvent. Subsequent to drying, these products are used directly in the subsequent olefination procedures. Another route to obtaining amine-containing phosphonium bromides is by treating an appropriate amino alcohol with triphenylphosphine hydrobromide (Helv. Chim. Acta, 61, pp.1708–1720, 1978). Some of the phosphonium bromides are commercially available.

Phosphonium bromides can also be prepared using diamines, usually with one of the amines protected, with t-BOC as one of the preferred protecting groups. Subsequent to Wittig olefination, the t-BOC group can be removed by conventional methods and the newly exposed amine can be further functionalized with an aminoacyl, dipeptidyl, or hydroxyalkanoyl group according to the following procedure. A dichloromethane solution of a N-protected amino acid, or N-protected dipeptide (t-BOC is one of the preferred protecting groups), or an O-protected hydroxyalkanoic acid (acetate is one of the preferred protecting groups), dicyclohexylcarbodiimide, and often a coupling agent, such as hydroxybenzotriazole, (all of which are present in equimolar amounts) is cooled to about 0° C. To the cold solution is added a macrolide derivative wherein T is $—CH=CH—(CH_2)_n—N(Z^4)(Z^5)$ where $Z^4$ is as defined above. $Z^5$ is $'R^6—N(R^7R^8)$ where $R^6$ and $R^8$ are as defined hereinabove and $R^7$ is hydrogen. The solution is allowed to warm to room temperature and stirring is continued for about 6 to 72 hours, followed by standard work-up procedures well-known to those skilled in the art. The crude product is isolated by conventional methods such as chromatography. The N-protected aminoacyl, N-protected dipeptidyl, or O-protected hydroxyalkanoyl derivative is then deprotected by conventional methods to yield desired products.

In all of the following syntheses if the bond between the $C_2$–$C_3$ positions of the macrolide is a double bond, then the reductive aminations are preferably carried out using the formic acid conditions described hereinbelow.

The particular reaction conditions and reagents used to synthesize a compound of formula I or II where T is $—CH(Z^8)N(Z^6)(Z^7)$ or

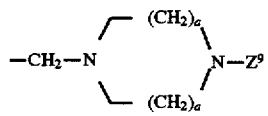

are dictated by the kind of amine that is used in the reaction. When a secondary amine of the formula $HN(Z^6)(Z^7)$, where $Z^6$ and $Z^7$ are not hydrogen and are as defined above for formula I or II is used in the reductive amination, the following procedure is utilized. A solution of a 3-deoxy derivative of the appropriate macrolide aldehyde is mixed with an excess, usually about 1.5 molar equivalent, of a secondary amine in a reaction inert solvent such as ethyl acetate. The reaction mixture is heated to about 60° C. to 80° C., preferably about 70° C., with stirring. A slight excess of formic acid, usually about 1.1 molar equivalent, is added dropwise to the reaction mixture and the temperature of the reaction mixture is lowered by about 5° C. The reaction is stirred for an additional four to seven hours, but usually for about five hours. The reaction is stopped by cooling to room temperature and the desired amino derivative of the 3-deoxy macrolide is isolated by standard techniques well known to those skilled in the art, such as column chromatography or crystallization.

The compounds of formula (I) or (II) where T is $—CH(Z^8)—N(Z^6)(Z^7)$ where $Z^8$ is hydrogen and $—N(Z^6)(Z^7)$ are derived from a primary amine employs the following method. A methanol solution of the 3-deoxy macrolide aldehyde is mixed with the appropriate amine and stirred at room temperature for approximately 30 minutes. The reaction mixture is then cooled to about 0° C. and an equimolar amount of glacial acetic acid is added to the mixture and the reaction allowed to stir. After about ten minutes of stirring, a methanol solution of sodium cyanoborohydride is added to the reaction mixture, and the resulting solution is stirred for about one hour at about 0° C. The reaction is stopped by warming to room temperature and concentrating the reaction mixture, and then the desired 3-deoxy macrolide derivative is isolated. A preferred method of accomplishing the same type of reaction is as follows. To a stirring solution of the 3-deoxy macrolide aldehyde in methanol is added the appropriate amine and the reaction is stirred for about 30 minutes. The solution is then cooled to about 0° C. and sodium borohydride is added to it. After stirring for about 2 hours, the solution is concentrated to near dryness and the desired compound is isolated by conventional methods well known in the art. The cyano derivative, where $Z^8$ is CN, is also produced in the reaction and can be isolated by standard techniques well known to those skilled in the art. The cyano derivatives of the compounds of formula (I) or (II) wherein T is —CH($Z^8$)—N($Z^6$)($Z^7$) where —N($Z^6$)($Z^7$) are as defined and $Z^8$ is CN, can also be synthesized separately by the following method. A solution of zinc iodide and an appropriate 3-deoxy macrolide aldehyde is made in methanol. Trimethylsilylcyanide is added to the methanol solution and is stirred for about 15 minutes then the appropriate amine is added and the solution is heated at about 40° C. for about 2 hours. The desired cyano derivative is isolated by standard methods well known in the art.

A primary amino derivative of the 3-deoxy macrolide, formed by the above method, can be further derivatized by N-methylating the secondary amino group which had been just added. This synthesis is carried out by suspending the secondary amino 3-deoxy macrolide derivative in water and then adding formic acid. To the resulting solution, a 38% solution of aqueous formaldehyde is added and the reaction mixture is heated to reflux temperature. The reaction mixture is stirred at reflux for about four to six hours, preferably about five hours. It is then cooled to room temperature and the desired compound is isolated.

When T is —CH($Z^8$)—N($Z^6$)($Z^7$) where —N($Z^6$)($Z^7$) is derived from a secondary amine the macrolide can be further functionalized with an amino acyl group according to the following procedure. A dichloromethane solution of a N-protected amino acid or N-protected dipeptide (t-BOC is one of the preferred protecting groups), or an O-protected hydroxyalkanoic acid (acetate is one of the preferred protecting groups), dicyclohexylcarbodiimide, often with a coupling agent, such as hydroxy-benzotriazole, (all of which are present in equimolar amounts) is cooled to about 0° C. To the cold solution is added a secondary amino compound of formula I or II; wherein $Z^6$ is hydrogen and $Z^7$ is as defined above. The solution is allowed to warm to room temperature and stirring is continued for about 48 to 72 hours. The crude product is isolated by conventional methods such as chromatography. The N-protected amino acyl, N-protected dipeptidyl or O-protected hydroxyalkanoyl derivative is deprotected by conventional methods to yield the desired product.

A compound of formula I or II wherein T is —CH($Z^8$)—N($Z^6$)($Z^7$) where —N($Z^6$)($Z^7$) is an aminoalkylamino, can be further derivatized at the terminal amine by an amino acyl group according to the following procedure. To a stirring solution of a compound of formula I or II having an aminoalkylamino group at the T-position in dimethylformamide is added an N-protected (t-BOC is preferred protecting group) amino acid hydroxysuccinimide ester, or N-protected dipeptide (t-BOC is one of the preferred protecting groups), or an O-protected hydroxyalkanoic acid (acetate is one of the preferred protecting groups), and the mixture is stirred for about 6 hours. The crude product is isolated by conventional methods such as silica gel chromatography. The N-protected amino acyl derivative, N-protected dipeptidyl or O-protected hydroxyalkanoyl derivative is deprotected by conventional methods to yield the desired products.

The compounds of this invention wherein T is —C(=O) ($Z^3$) are synthesized according to the following procedure. The 3-deoxy macrolide aldehyde is oxidized to the carboxylic acid. The intermediate carboxylic acid derivative of the 3-deoxy macrolides is then coupled with a variety of amines to form amide derivatives. For example, a suitably protected 3-deoxy macrolide, protected as the 2'-acetate, is treated with approximately 1.3 equivalents of sodium chlorite in the presence of approximately 1.3 equivalents of sodium phosphate monobasic and an excess of 2-methyl-2-butene, about 7.0 equivalents. This oxidation step is usually carried out at ambient room temperature (20°–25° C.) using a 3:1 mixture of acetonelbutanol as the solvent (0.3 to 0.5 molar concentration). In order to form the amide derivatives, the carboxylic acid is coupled with primary or secondary amines in the presence of about 1.1 equivalents of diethyl cyanophosphate and about 1.1 equivalents of triethylamine at about 0° C. using anhydrous DMF as the solvent (0.1 molar concentration). The reaction is worked up by pouring it into saturated aqueous $NaHCO_3$ and extracting with EtOAc. The isolated product is purified by flash chromatography to afford the amide derivative. The 2'-acetate group can be removed by dissolving the above product in methanol (MeOH). The resulting solution is then stirred at room temperature (20°–25° C.) for about 18–24 hours. The reaction mixture is concentrated under reduced pressure to afford the deprotected amide derivative of the 3-deoxy macrolide.

Alternatively, compounds of this invention wherein T is —C(=O)($Z^3$) are synthesized from the carboxylic acid of the 2'-acetate of the 3-deoxy macrolides according to the following method. To a 0.1M solution of the carboxylic acid in a polar aprotic solvent such as $CH_2Cl_2$, which has been cooled to about 0° C., is added about 5 equivalents of either a primary or a secondary amine. Propylphosphonic anhydride (1.4 equivalents) is added as a 50% solution in $CH_2Cl_2$ and the reaction is allowed to warm to ambient temperature. After stirring for about 1–5 hours the reaction mixture is concentrated in vacuo and then redissolved in MeOH to cleave the 2'-acetate. The reaction mixture is concentrated after stirring overnight and extracted from a basic aqueous solution to provide the 3-deoxy macrolide amide.

The compounds of this invention wherein T is —$CH_2$—N($Z^2$)(C=O)—$(CH_2)_a$—$Z^3$ are readily prepared by the following method. The desired 3-deoxy macrolide is reductively aminated with an amine in the presence of sodium triacetoxyborohydride, or formic acid if the bond between C2 and C3 of the 3-deoxy macrolide is a double bond, as described hereinabove. The resulting aminated macrolide is then coupled with the desired carboxylic acid according to one of the coupling methods described hereinabove.

The amino amide compounds of this invention wherein T is —$CH_2$—N(B)($CH_2$)$_a$—C(=O)($Z^3$) or —$CH_2$—N(B) ($CH_2$)$_g$—N(B)($CH_2$)$_a$—C(=O)($Z^3$) can be synthesized by the following two general methods. Certain amino amide fragments are available commercially or can be prepared from an amino acid such as glycine, sarcosine or β-alanine and a variety of amines by the same methods described hereinabove for the carboxylic acid derivatives of the 3-deoxy macrolides described in this invention. The amine moiety of the amino acid portion can then be coupled with the 3-deoxy macrolide aldehyde by reductive amination methods known to those skilled in the art. The following method can be employed. The desired 3-deoxy macrolide aldehyde, an amine, usually about 1.5 equivalents, and acetic acid are stirred in a reaction-inert solvent such as methylene chloride for about 30 to 60 minutes. After cooling to about 0° C., powdered sodium sulfate (about 10 equivalents) and sodium triacetoxyboro-hydride, orformic acid if the bond between C2 and C3 of the 3-deoxy macrolide is a double bond, about 1.1 equivalents, are added and the reaction solution is stirred at ambient temperature for about 1 to 12 hours. The desired amino 3-deoxy macrolide derivative is then isolated by standard techniques well known to those of ordinary skill in the art, such as column chromatography or crystallization. Alternatively, the reductive amination can first be performed with the 3-deoxy macrolide aldehyde and a protected amino acid. Following deprotection, the acid can then be coupled to a variety of amines by the methods described hereinabove. Further, the reductive amination is preferably carried out with formic acid when the bond between C2–C3 of the macrolide is a double bond, as described hereinabove.

The pharmaceutically acceptable acid addition salts of the 3-deoxy macrolide derivatives can be obtained by the following general procedure. For example, the HCl salts can be isolated by dissolving the 3-deoxy macrolide derivative in a methanolic HCl solution and then evaporating the volatile components to yield the desired salt. The methanolic HCl solution can be prepared by mixing acetyl chloride with methanol. In addition to the HCl salts, other preferred pharmaceutically acceptable acid addition salts include citrate, phosphate, sulfate, methanesulfonate, benzenesulfonate, palmitate, succinate, lactate, malate, tartrate, fumerate and stearate salts. All of such salts are prepared in a method analogous to the method used to form the HCl salt.

The antibacterial activity of the compounds of the present invention against bacterial pathogens is demonstrated by the compound's ability to inhibit growth of *Pasteurella multocida* and/or *Pasteurella haemolytica*. The following procedures are typical assays. Assay I is utilized to test for activity against *Pasteurella multocida* and Assay II is utilized to test for activity against *Pasteurella haemolytica*.

Assay I (*P. multocida*)

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 µl of dimethylsulfoxide (DMSO). Dilutions of the test compound are prepared using uninoculated BHI broth. The concentrations of the test compound used range from 200 µg/ml to 0.098 µg/ml by two-fold serial dilutions. The *P. multocida* inoculated BHI is diluted with uninoculated BHI broth to make a $10^4$ cell suspension per 200 µl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay II (*P. haemolvtica*)

This assay is based on the agar dilution method using a Steers Replicator. Two to five colonies isolated from an agar plate are inoculated into BHI broth and incubated overnight at 37° C. with shaking (200 rpm). The next morning, 300 µl of the fully grown *P. haemolytica* preculture are inoculated into 3 ml of fresh BHI broth and are incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 µl of the *P. haemolytica* culture is inoculated onto BHI agar plates containing the various concentrations of the test compound using a Steers Replicator and incubated for 18 hours at 37° C. Initial concentrations of the test compound range from 100–200 µg/ml. The MIC is equal to the concentration of the test compound exhibiting 100% inhibition of growth of *P. haemolytica* as determined by comparison with an uninoculated control.

The in vivo activity of the compounds of formula (I) or (II) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or per os. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

To implement the methods of this invention, an effective dose of a compound of formula (I) or (II) or a pharmaceutically acceptable salt thereof is administered to a susceptible or infected animal by parenteral (i.v., i.m. or s.c.), oral or topical route. The effective dose will vary with the severity of the disease, and the age, weight and condition of the animal. However, the daily dose will usually range from about 0.25 to about 150 mg/kg, preferably from about 0.25 to about 25 mg/kg.

A suitable vehicle for administering the dose parenterally is a solution of the compound in sterile water, or a solution of the compound in a solvent comprising at least 50% water and a pharmaceutically acceptable cosolvent or cosolvents such as methanol, ethanol, isopropyl alcohol, propylene glycol, glycerol, carbonate esters like diethyl carbonate, dimethyl sulfoxide, N,N-dimethylformamide, N,N-dimethylacetamide and 1-methyl-2-pyrrolidinone. Suspensions are also suitable vehicles for administering the compounds of this invention. The suspending medium can be, for example, aqueous carboxymethyl cellulose, inert oils such as peanut oil, highly refined mineral oils and aqueous polyvinylpyrrolidone. Suitable physiologically acceptable adjuvants may be necessary to maintain the compound in suspension. These adjuvants may be chosen from among thickeners such as carboxymethyl cellulose, polyvinylpyrrolidone, gelatin, and the alginates. Surfactants are also useful as suspending agents. These surfactants include: lethicin, alkylphenol polyethylene oxide adducts, naphthalenesulfonates, alkylbenzenesulfonates and polyoxyethylene sorbitan esters. Agents affecting surface tension can also help in making useful suspensions. Such agents include silicone anti-foams, sorbitol, and sugars. For intravenous use the total concentration of solutes should be controlled to render the preparation isotonic.

The present invention is illustrated by the following examples, but is not limited to the details thereof. High Performance Liquid Chromatography (HPLC) retention times of the products of this invention are determined on a Zorbax RX®, 5 micron C8 column (4.6 mm ID×15 cm length) from Dupont (available from Mac-Mod Analytical Inc., 127 Commons Court, Chadds Ford, Pa. 19317 1-800-441-7508). A 45:55 (vol:vol) mixture of acetonitrile to aqueous 50 millimolar ammonium acetate is used as the eluant. The column temperature is maintained at 40° C. and the flow rate is 1.0 ml per minute. Samples are dissolved in the eluant (2 mg/ml) and are injected (70 µl) into a Hewlett-Packard 1090 high performance liquid chromatography instrument; peaks corresponding to the sample input are detected by ultraviolet spectroscopy at either 254 or 280 nm.

EXAMPLE 1

3,4'-Dideoxy-20-deoxo-20-(hexahydroazepin-1-yl)-5-O-mycaminosyltylonolide

Method A (using HCO₂H)

A mixture of 3,4'-dideoxy-OMT (150 mg; 0.265 mmoles) and hexamethyleneimine (40 mg; 0.40 mmoles) was dissolved in ethyl acetate (4 mL) and heated to a gentle reflux for about 1.0 hr. The mixture was cooled slightly and formic acid (18 mg; 0.39 mmoles) was added. The reaction mixture was again heated to gentle reflux for about 0.5 hrs, at which time it was judged to be complete by HPLC. The mixture was cooled to room temperature and evaporated to a residue (180 mg). The desired product was purified from this residue by preparative HPLC:

Column: Kromasil C₄ (50×250 mm) (Available from Bodman Industries, Aston Pa. 19014, 1-800-241-8774).

Mobile phase: linear gradient; buffer/ACN from 84/16 to 77/23 in 140 min buffer=50 mM KH₂PO₄ at pH=3.0

Flow: 80 ml/min

Detection: UV at 290 nm

Fraction volume: 125 mL

Fractions containing the title compound were combined and evaporated to give a white solid (109 mg; 63%); FAB-MS: m/e=649; HPLC retention time: 5.20 min.

Method B (using NaBH(OAc)₃)

To a solution of 3,4'-dideoxy-5-O-mycaminosyltylonolide (400 mg, 0.71 mmol) and hexamethyleneimine (0.096 mL, 0.85 mmol) in 3.6 mL of CH₂Cl₂ at room temperature was added powdered anhydrous Na₂SO₄ (1.0 g, 7.1 mmol). After stirring at room temperature for about one hour, the mixture was heated to reflux for about one hour. Upon cooling to room temperature, acetic acid (0.2 mL, 3.6 mmol) was added and stirring was continued for about one hour at room temperature. The reaction was then cooled to about 0° C., and NaBH(OAc)₃ (180 mg, 0.85 mmol) was added in one portion. The reaction was allowed to warm slowly to room temperature and stirred overnight. The mixture was filtered and the filtrate concentrated. The residue was dissolved in CHCl₃, and washed with aqueous saturated NaHCO₃ and saturated sodium chloride. The organic layer was dried over anhydrous sodium sulfate, filtered, and then evaporated under reduced pressure to afford 400 mg of product (87% yield, 91.5% pure by HPLC).

EXAMPLES 2–23

The compounds of Examples 2–23 have the general formula shown below and were synthesized according to a method analogous to the method indicated.

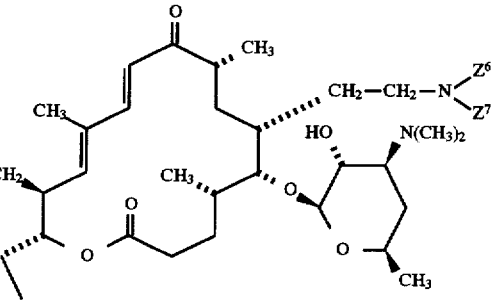

| Ex. No. | NZ⁶Z⁷ | Prep'n. Method | Mass. Spec. | HPLC (min.) |
|---|---|---|---|---|
| 2 | N-methyl-N-cyclohexylamino | A | 664 | 6.80 |
| 3 | dimethylamino | A | 596 | 3.84 |
| 4 | 2-fluoroethylamine | B | 614 | 4.37 |
| 5 | dipropylamine | A | 652 | 6.46 |
| 6 | N-methyl-N-propylamino | B | 624 | 4.93 |
| 7 | N-[3-(dimethylamino)-propyl]-N-methylamino | A | 667 | 3.66 |
| 8 | 4-methylpiperazino | A | 651 | 4.62 |
| 9 | 2,2-dimethyl-3-hydroxy-propylamino | B | 654 | 4.66 |
| 10 | azetidino | B | 608 | N.T. |
| 11 | 3-azabicyclononan-3-yl | B | 676 | N.T. |
| 12 | N-methyl-N-2-hydroxy-ethylamino | B | 626 | N.T. |
| 13 | propylamino | B | 610 | N.T. |
| 14 | 3-hydroxypropylamino | B | 626 | N.T. |
| 15 | 2-spirocyclopentyl-3-hydroxy-propylamino | B | 680 | N.T. |
| 16 | 2,5-(dihydroxy)cyclo-hexylamino | B | 682 | N.T. |
| 17 | 3-amino-2,2-dimethyl-propylamino | B | 653 | N.T. |
| 18 | pyrrolidino | A | 621 | 4.15 |
| 19 | piperidino | A | 635 | N.T. |
| 20 | 4-hydroxypiperidino | A | 651 | 3.66 |
| 21 | morpholino | A | 637 | 6.26 |
| 22 | 3,4-dehydropiperidino | A | 633 | 4.80 |
| 23 | 3-hydroxypiperidino | A | 651 | N.T. |

N.T. = Not taken.

EXAMPLES 24–25

The compounds of Examples 24–25 have the general formula shown below and were synthesized according to a method analogous to the method indicated.

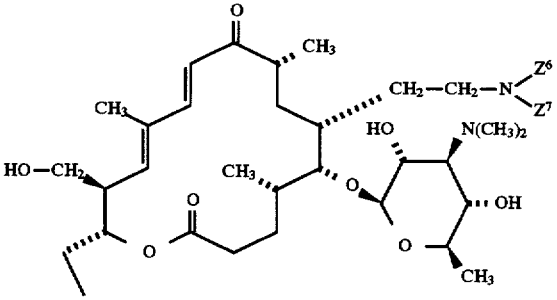

| Ex. No. | NZ⁶Z⁷ | Prep'n Method | Mass Spec. |
|---|---|---|---|
| 24 | hexahydroazepin-1-yl | B | 666 |

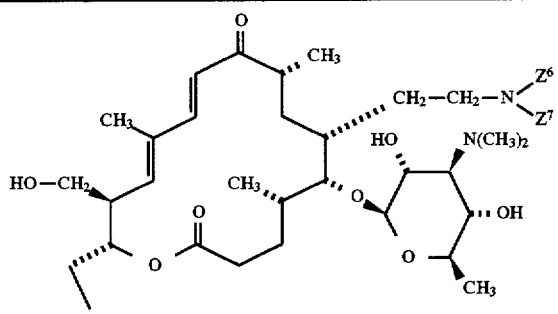

| Ex. No. | NZ⁶Z⁷ | Prep'n Method | Mass Spec. |
|---|---|---|---|
| 25 | 2,2-dimethyl-3-hydroxy-propylamino | B | 670 |

EXAMPLES 26–31

The compounds of Examples 26–31 have the general formula shown below and were synthesized according to a method analogous to the method indicated.

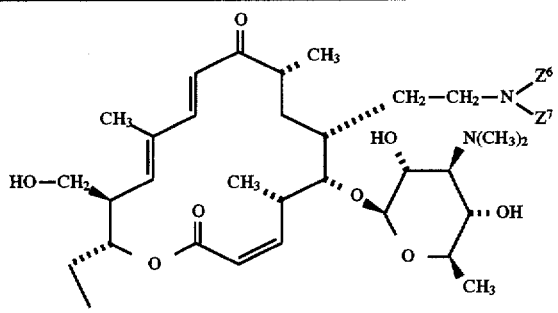

| Ex. No. | NZ⁶Z⁷ | Prep'n Method* | Mass. Spec. |
|---|---|---|---|
| 26 | 2,2-dimethyl-3-hydroxy-propylamino | B | 668 |
| 27 | hexahydroazepin-1-yl | A (EtOAc) | 663 |
| 28 | dimethylamino | A (THF) | 609 |
| 29 | dipropylamino | B | 666 |
| 30 | N-[3-(dimethylamino)propyl]-N-methylamino | B | 680 |
| 31 | 3-azabicyclononan-3-yl | A (EtOAc) | 689 |

*The solvent used for the reaction is indicated in the parenthesis.

Preparation 1

3-Deoxy-5-O-mycaminosyltylonolide

To a solution of the bis-ethylene ketal of 5-O-mycaminosyltylonolide (OMT) (2.120 g, 3.091 mmol) (prepared as described in Bull. Chem. Soc. Jpn., 1992, 65, p. 3405) in 10 mL of DMF was added dimethylthexylsilyl chloride (829 mg, 4.636 mmol) and imidazole (421 mg, 6.182 mmol). The reaction mixture was stirred at room temperature under nitrogen overnight. Solvent was removed under vacuum and the residue was taken up in 60 mL CHCl₃ and washed with 60 mL water. The organic layer was dried over Na₂SO₄, filtered, evaporated, and flash chromatographed over silica gel (8% MeOH/CH₂Cl₂ with 0.2% NH₄OH). Appropriate fractions were pooled and evaporated to dryness to yield 2.600 g (55.4%) of the dimethylthexylsilyl-diketal intermediate.

To a solution of the dimethylthexylsilyl-diketal intermediate (2.148 g, 2.59 mmol) in 20 mL acetonitrile was added acetic anhydride (0.635 g, 6.22 mmol). The reaction mixture was stirred at room temperature under nitrogen overnight. Solvent was removed under vacuum and the residue was taken up in 100 mL toluene and washed with saturated NaHCO₃ solution. The organic layer was dried over MgSO₄, filtered, and evaporated to dryness to yield 1.978 g (83.7%) of the bis-acetylated intermediate. MS LSIMS: 912.

To a solution of the bis-acetylated intermediate (1.412 g, 1.548 mmol) in 2 mL anhydrous pyridine was added methanesulfonyl chloride (0.433 g, 3.870 mmol). The cloudy reaction mixture was stirred at room temperature under nitrogen for about 3 hours. The solution was added to 50 mL saturated NaHCO₃ solution. The mixture was extracted several times with toluene. The combined organic layers were dried over MgSO₄, filtered, and evaporated to dryness to yield 1.461 g (95.3%) of the mesylated intermediate.

To a solution of the mesylated intermediate (1.420 g, 1.434 mmol) in 30 mL methanol was added 10 mL concentrated NH₄OH. The reaction mixture was stirred at room temperature for about 2.5 hours then heated to 50° C. overnight. Solvent was removed under reduced pressure and the residue was partitioned between chloroform and saturated NaCl solution. The organic layer was dried over Na₂SO₄, filtered and evaporated to dryness to give 1.101 g (94.8%) of the 2,3-trans olefin intermediate.

To a solution of the 2,3-trans olefin intermediate (0.935 g, 1.154 mmol) in 33 mL of methanol was added K₂CO₃ (0.475 g, 3.437 mmol) and Raney Nickel (about 0.5 mL suspension in water). The mixture was hydrogenated on a Parr shaker at 15 psi for about 10 minutes. The catalyst was quickly filtered off and the filtrate evaporated under reduced pressure. The residue was taken up in methylene chloride and washed with saturated NaHCO₃ solution. The organic layer was dried over Na₂SO₄, filtered, and evaporated to dryness to yield 0.914 g (98%) of the desired protected intermediate.

The protected intermediate was taken up in 20 mL of 0.25 N HCl and 5 mL acetonitrile and stirred at room temperature for about 2 hours. The mixture was poured into 200 mL saturated NaHCO₃ solution. The cloudy mixture was extracted several times with chloroform. The combined organic layers were dried over Na₂SO₄, filtered, evaporated to dryness and flash chromatographed over silica gel (5% MeOH/CHCl₃ with 0.5% NH₄OH). Appropriate fractions were pooled and evaporated to dryness to yield 0.679 g (quantitative) of the title compound as a white solid foam. MS EI 581.4.

Preparation 2

3-Deoxy-2,3-Didehydro-5-O-mycaminosyltylonolide

To a solution of OMT (5.00 g, 8.36 mmol) in 56 mL EtOH at room temperature was added powdered 4A molecular sieves and p-toluenesulfonic acid (2.38 g, 12.54 mmol). Stirring was continued at room temperature for about 5 hours at which time the reaction was quenched with Et₃N (1.6 mL, 11.7 mmol). The reaction mixture was filtered and concentrated to dryness. The residue was dissolved in CH₂Cl₂ and washed with aqueous saturated NaHCO₃ and brine. The organic layer was dried over Na₂SO₄, filtered and concentrated to provide 3.4 g of diethyl acetal intermediate (61% yield).

To a solution of the diethyl acetal intermediate (7.99 g, 11.9 mmol) in 39.6 mL DMF was added imidazole (1.62 g, 23.8 mmol), followed by dimethylthexylsilyl chloride (3.5 mL, 17.85 mmol). After stirring overnight at room temperature under nitrogen, additional imidazole (810 mg, 11.9 mmol) and dimethylthexylsilyl chloride (1.75 mL, 8.9 mmol) was added. The reaction was stirred for about an additional 5 hours at which time TLC analysis (89:10:1 CHCl₃:MeOH: NH₄OH) indicated that starting material had been consumed. The solvent was removed under vacuum. The residue was dissolved in CH₂Cl₂ and washed with water and brine. The organic layer was dried over Na₂SO₄, filtered and concentrated to a yellow oil which was chromatographed over silica gel (2% MeOH/CHCl₃ with 0.1% NH₄OH) to yield 6.2 g of clean 23-dimethylthexylsilyl-20-diethyl acetal intermediate (64% yield). MS (particle beam) 815.

To the 23-dimethylthexylsilyl-20-diethyl acetal intermediate (7.6 mmol) in 38 mL acetonitrile was added acetic anhydride (1.58 mL, 16.7 mmol). The reaction was stirred overnight at room temperature under nitrogen. The solvent was removed under vacuum and the residue was dissolved in CH₂Cl₂, and washed with aqueous saturated NaHCO₃ and brine. The organic layer was dried over Na₂SO₄, filtered and evaporated to dryness to yield 6.5 g diacetate intermediate (96% yield). MS (particle beam) 899.

To a solution of the diacetate intermediate (7.2 mmol) in pyridine (72 mL) was added methanesulfonyl chloride (1.39 mL, 18 mmol). The cloudy reaction mixture was stirred at room temperature under nitrogen for about 5 hours. TLC analysis (cyclohexane:acetone 3:1) indicated that the starting material had been completely consumed. The solvent was removed under vacuum and the residue was dissolved in toluene. The toluene solution was washed with aqueous saturated NaHCO₃ and brine. The organic layer was dried over Na₂SO₄, filtered and concentrated to 7.0 g of the 3-O-mesyl intermediate (99% yield). MS (particle beam) 977, 881.

To a solution of the 3-O-mesyl intermediate in 180 mL of methanol was added dropwise with vigorous stirring, concentrated NH₄OH (90 mL). The gummy precipitate which formed gradually dissipated. The reaction was stirred at room temperature for about 3 hours. The solvent was removed under vacuum. The residue was redissolved in methanol (90 mL) and the reaction was heated to 50° C. overnight. The solvent was removed under vacuum. The residue was dissolved in CHCl₃ and washed with water and brine. The organic layer was dried over Na₂SO₄, filtered and concentrated to 5.0 g off-white 2,3-trans olefin intermediate (88% yield).

To the 2,3-trans olefin intermediate in acetonitrile (80 mL) was added dropwise 0.25 N aqueous HCl (320 mL). The reaction was stirred at room temperature for about 4.5 hours, at which time the reaction mixture was adjusted to pH 9 with aqueous saturated NaHCO₃. This mixture was stirred for about 30 minutes at room temperature and then extracted with CHCl₃. The organic layer was washed with brine, filtered and concentrated. The residue (3.5g) was chromatographed over silica gel (2% MeOH/CHCl₃ with 0.25% aqueous (NH₄OH). The appropriate fractions were pooled and concentrated to yield 1.4 g of the title compound as a white foam (38% yield). High Res. MS EI 579.3047.

Preparation 3

3,4'-Dideoxy-5-O-mycaminosyltylonolide

This material was prepared as described in *Bull. Chem. Soc. Jpn.*, 1992, 65, p. 3405.

We claim:
1. A compound of formula I or II

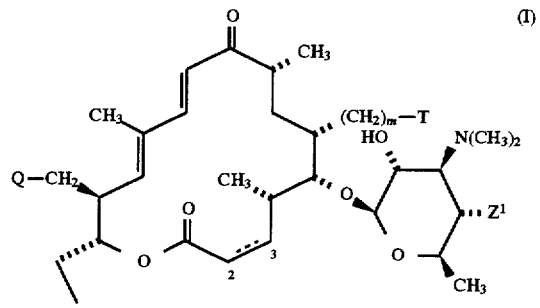

or

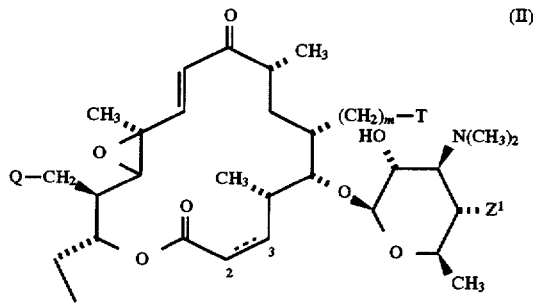

or a pharmaceutically acceptable salt thereof
wherein m is 1 or 2;
Z¹ is H, OH or mycarosyloxy;
represents a single or a double bond wherein the double bond results in either the cis or trans geometry;
Q is selected from the group consisting of H, OH, fluoro, chloro, bromo, iodo, OX¹,

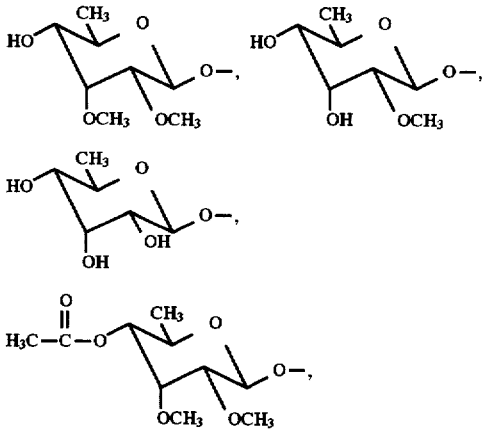

azetidin-1-yl, pyrrolidin-1-yl, piperidin-1-yl, 3,3-dimethylpiperidin-1-yl, hexahydroazepin-1-yl, octahydroazocin-1-yl, octahydroindol-1-yl, 1,3,3a,4,7,7a-hexahydroisoindol-2-yl, decahydroquinol-1-yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholino, 2,6-dimethylmorpholin-4-yl, thiomorpholino, and —NX²X³;
X¹ is selected from the group consisting of optionally substituted alkyl having 1 to 4 carbons, optionally substituted cycloalkyl having 4 to 8 carbon atoms, and an optionally substituted aryl, aralkyl or heteroaryl group selected from the group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl;

where the optionally substituted aryl, aralkyl and heteroaryl groups are optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion;

$X^2$ and $X^3$ are each independently selected from the group consisting of hydrogen, alkyl having 1 to 4 carbons, hydroxyalkyl having 2 to 4 carbons, cycloalkyl having 3 to 8 carbons, alkenyl having 3 or 4 carbons, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion;

T is $-C(=O)(Z^3)$, $-CH_2-N(B)(CH_2)_a-C(=O)(Z^3)$, $-CH_2-N(Z^2)(C=O)-(CH_2)_a-Z^3$, $-CH_2-N(B)(CH_2)_g-N(B)(CH_2)_a-C(=O)(Z^3)$, $-CH=CH-(CH_2)_n-N(Z^4)(Z^5)$, $-CH(Z^8)N(Z^6)(Z^7)$,

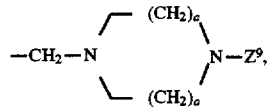

$-CH_2-N(Z^{12})(SO_2Z^{13})$, $-CH_2-N(Z^{12})(C(=O)-Z^{14}-Z^{13})$, $-CH_2-N(Z^{12})(CH_2)_g-N(Z^{15})(C(=O)-Z^{14}-Z^{13})$ or $-CH_2-N(Z^{12})(CH_2)_g-N(Z^{15})(SO_2-Z^{13})$;

wherein n is an integer from 1 to 4;

B for each occurrence is independently selected from the group consisting of hydrogen, $(C_1-_4)$alkyl, an aminoacyl group and a dipeptidyl group;

$Z^2$ is hydrogen or $(C_1-C_4)$alkyl;

$Z^3$ is $-N(R^1R^2)$, $-NH-CH(R^3)-(CH_2)_e-COOR^4$ or $-NH-CH(R^3)-(CH_2)_e-C(=O)-NH-(CH_2)_f-COOR^4$;

$R^1$ and $R^2$ are each independently selected from the group consisting of hydrogen, methyl, optionally substituted alkyl having 2 to 6 carbons, optionally substituted cycloalkyl having 3 to 8 carbons, aminoalkyl having 2 to 6 carbons, hydroxyalkyl having 2 to 6 carbons, N-alkylamino-alkyl having 1 to 4 carbons in the alkylamino portion and 2 to 4 carbons in the alkyl portion, optionally substituted benzyl, optionally substituted phenyl, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion, $-(CH_2)_g$-morpholino, $-(CH_2)_g$-piperidino, $-(CH_2)_g$-pyrrolidino, $-(CH_2)_g$-azetidin-1-yl, and $-(CH_2)_g$-hexahydroazepin-1-yl;

or $R^1$ and $R^2$ are taken together with the nitrogen to which they are attached and form $Z^{100}$;

$R^3$ corresponds to just the side chain portion of amino acids and for each occurrence is independently selected from the side chain of the group of amino acids consisting of the D- or L-form, when applicable, of alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, tryptophan, tyrosine, valine, β-alanine, β-lysine, α,α-dimethylglycine, α-aminobutyric acid, 4-hydroxyphenylglycine, phenylglycine, α,γ-diaminobutyric acid, ornithine and homoserine;

e is 0 or 1, provided that when e is 1 then $R^3$ corresponds to the side chain of β-lysine or β-alanine;

f is 0 or 1, provided that when f is 1 then $R^3$ corresponds to the side chain of β-lysine or β-alanine;

$R^4$ is H, alkyl having 1 to 4 carbons or benzyl;

$Z^4$ is selected from the group consisting of hydrogen, an aminoacyl group, a dipeptidyl group, alkenyl having 3 to 5 carbons provided that the double bond is not adjacent to the nitrogen to which $Z^4$ is attached, alkynyl having 3 to 5 carbons provided that the triple bond is not adjacent to the nitrogen to which $Z^4$ is attached, hydroxyalkyl having 2 to 4 carbons in the alkyl portion, $Q^{10}$, $Q^{20}$, $Q^{30}$, and alkoxyalkyl having 2 to 4 carbons in the alkyl portion and 1 to 4 carbons in the alkoxy portion;

$Z^5$ is selected from the group consisting of hydrogen, alkenyl having 3 to 5 carbons provided that the double bond is not adjacent to the nitrogen to which $Z^5$ is attached, alkynyl having 3 to 5 carbons provided that the triple bond is not adjacent to the nitrogen to which $Z^5$ is attached, hydroxyalkyl having 2 to 4 carbons in the alkyl portion, $Q^{10}$, $Q^{20}$, $Q^{30}$, alkoxyalkyl having 2 to 4 carbons in the alkyl portion and 1 to 4 carbons in the alkoxy portion and $-R^6-N(R^7R^8)$;

$Q^{10}$ for each occurrence is independently

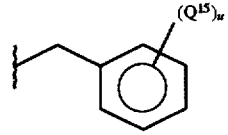

where u is an integer from 1 to 5 and $Q^{15}$ for each occurrence is independently selected from the group consisting of $(C_1-C_4)$alkyl, $(C_1-C_4)$alkoxy, fluoro, chloro, bromo, iodo, nitro, amino, cyano, hydroxy, trifluoromethyl and carboalkoxy having 1 to 4 carbons;

$Q^{20}$ for each occurrence is independently an optionally substituted $(C_1-C_4)$alkyl, optionally substituted with a substituent selected from the group consisting of hydroxy, cyano, N-alkylamino having 1 to 5 carbons and N,N-dialkylamino having a total of 2 to 6 carbons;

$Q^{30}$ for each occurrence is independently

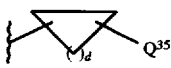

where d is an integer from 1 to 5 and $Q^{35}$ is selected from the group consisting of hydroxy, cyano, N-alkylamino having 1 to 5 carbons and N,N-dialkylamino having a total of 2 to 6 carbons;

$R^6$ is $(C_2-C_4)$alkylene;

$R^7$ is selected from the group consisting of hydrogen, alkyl having 1 to 4 carbons, cycloalkyl having 3 to 8 carbons and alkoxyalkyl having 2 to 4 carbons in the alkyl portion and 1 to 4 carbons in the alkoxy portion;

$R^8$ is selected from the group consisting of alkyl having 1 to 4 carbons, an optionally substituted hydroxyalkanoyl having 1 to 6 carbons, an aminoacyl group and a dipeptidyl group, wherein the optionally substituted hydroxyalkanoyl group is optionally substituted with an optionally substituted phenyl group;

or $R^7$ and $R^8$ are taken together with the nitrogen to which they are attached and form a cyclic amine having 3 to 6 carbon atoms;

or $Z^4$ and $Z^5$ are taken together with the nitrogen to which they are attached and form $Z^{100}$;

$Z^6$ is an aminoacyl group, a dipeptidyl group or is independently selected from the same group as defined for $R^1$;

$Z^7$ is independently selected from the same group as defined for $R^1$ or from the group consisting of

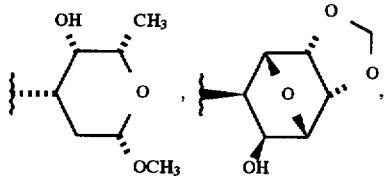

$—[(CH_2)_g—R^{12}]_g—CH_2)_g—N(Z^{16})_2$ and $—R^9—N(R^{10}R^{11})$;

wherein q is 1, 2 or 3;

$R^9$ is $(C_2—C_4)$alkylene optionally substituted with $(C_1-C_4)$alkyl or hydroxy provided that the hydroxy can only be attached to the C2 of the alkylene group when the alkylene is three carbon atoms long or to the C3 of the alkylene group when the alkylene is four carbon atoms long;

$R^{10}$ is selected from the group consisting of hydrogen, methyl and ethyl;

$R^{11}$ is selected from the group consisting of an optionally substituted hydroxyalkanoyl having 1 to 6 carbons, an amino acyl group, and dipeptidyl group, the optionally substituted hydroxyalkanoyl group is optionally substituted with an optionally substituted phenyl;

or $R^{10}$ and $R^{11}$ are taken together with the nitrogen to which they are attached and form $Z^{100}$;

$R^{12}$ is S or O;

$Z^{16}$ for each occurrence is independently selected from the group consisting of an aminoacyl group, dipeptidyl group and the same group of substituents as is defined hereinbelow for $Z^{12}$, $Z^{13}$ and $Z^{15}$;

or $Z^6$ and $Z^7$ are taken together with the nitrogen to which they are attached and form $Z^{100}$;

$Z^8$ is H or CN;

$Z^9$ is $(C_1-C_6)$alkyl, amino acyl group, dipeptidyl group, hydroxyalkanoyl having 1 to 6 carbons, aminoalkyl having 2 to 6 carbons, hydroxyalkyl having 2 to 4 carbons, N-alkylaminoalkyl having 1 to 4 carbons in the alkylamino portion and 2 to 4 carbons in the alkyl portion, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion, $—CO—Z^{14}—Z^{13}$ or $—SO_2—Z^{13}$;

$Z^{12}$, $Z^{13}$ and $Z^{15}$ for each occurrence are each independently selected from the same group as defined for $R^1$, provided that $Z^{13}$ is hydrogen only when $Z^{14}$ is NH;

$Z^{14}$ for each occurrence is independently O or NH;

a for each occurrence is independently 1 or 2;

for each occurrence of the amino acyl group and dipeptidyl group, the amino acyl group and the amino acyl groups of the dipeptidyl group are independently selected from the group consisting of the D- or L-form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

for each occurrence of an optionally substituted alkyl or optionally substituted cycloalkyl, the optionally substituted alkyl or optionally substituted cycloalkyl is independently selected from an optionally substituted alkyl or optionally substituted cycloalkyl optionally substituted with 1, 2 or 3 substituents independently selected from the group consisting of hydroxy, cyano, fluoro, trifluoromethyl, optionally substituted amino, optionally substituted N-alkylamino having 1 to 4 carbons, N,N-dialkylamino having a total of 2 to 6 carbons, N-(hydroxyalkyl)amino having 2 to 4 carbons, N,N-bis(hydroxyalkyl)amino wherein each alkyl portion has 2 to 4 carbons, alkoxy having 1 to 4 carbons, alkoxycarbonyl having 1 to 4 carbons in the alkoxy portion, N,N-dialkylaminoalkoxy having a total of 2 to 6 carbons in the dialkylamino portion and 2 to 4 carbons in the alkoxy portion, alkoxyalkoxy having 1 to 4 carbons in each of the alkoxy portions, alkoxyalkoxyalkoxy having 1 to 4 carbons in each of the alkoxy portions, spirocycloalkyl having 4 to 6 carbons,

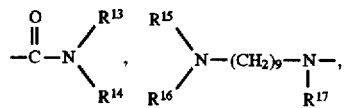

-continued

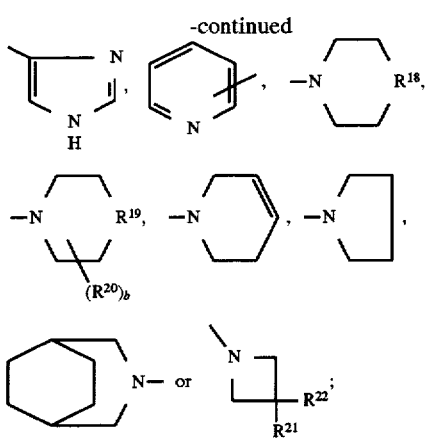

wherein the optionally substituted amino and the optionally substituted N-alkylamino are each independently optionally mono-substituted with an aminoacyl group or a dipeptidyl group;

$R^{13}$ and $R^{14}$ are each independently selected from the group consisting of hydrogen and alkyl having 1 to 4 carbons;

or $R^{13}$ and $R^{14}$ are taken together with the nitrogen to which they are attached and form $Z^{100}$;

$R^{15}$, $R^{16}$, and $R^{17}$ are each independently selected from the group consisting of hydrogen, $(C_1-C_4)$alkyl, an aminoacyl group and a dipeptidyl group;

$R^{18}$ is NH, S, N-$(C_1-C_4)$alkyl, N-(amino acyl group), or N-(dipeptidyl group);

$R^{19}$ is selected from the group consisting of C, CH, $CH_2$, N and NH;

$R^{20}$ is alkyl having 1 to 4 carbons or —$COOR^{21}$;

$R^{21}$ for each occurrence is independently H or alkyl having 1 to 4 carbons;

$R^{22}$ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or $R^{21}$ and $R^{22}$ are taken together and form an oxo group;

$Z^{100}$ for each occurrence is independently selected from the group consisting of

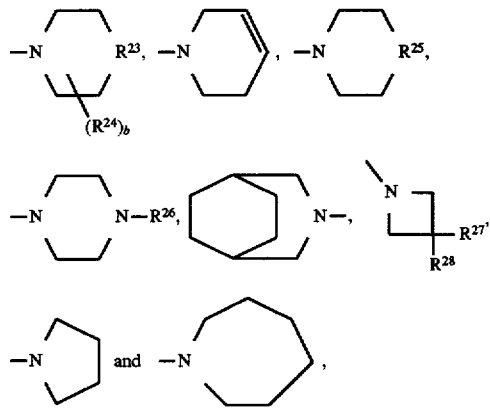

where $R^{23}$ is selected from the group consisting of C, CH, $CH_2$, N, NH, N(amino acyl) or N(dipeptidyl group);

$R^{24}$ is alkyl having 1 to 4 carbons, —CO—$(C_1-C_4)$ alkyl or —COO—$(C_{1-4})$alkyl;

$R^{25}$ is O or S;

$R^{26}$ is selected from the group consisting of alkyl having 1 to 4 carbons, an optionally substituted hydroxyalkanoyl having 1 to 6 carbons, an amino acyl group and a dipeptidyl group,
wherein the optionally substituted hydroxyalkanoyl group is optionally substituted with an optionally substituted phenyl group;

$R^{27}$ is H or alkyl having 1 to 4 carbons;

$R^{28}$ is H, alkyl having 1 to 4 carbons, hydroxy, alkoxy having 1 to 3 carbons, amino, N-alkylamino having 1 to 4 carbons or N,N-dialkylamino having a total of 2 to 6 carbons;

or $R^{27}$ and $R^{28}$ are taken together and form an oxo;

g for each occurrence is independently 2, 3, or 4;

b for each occurrence is independently 0, 1 or 2; and for each occurrence of the optionally substituted phenyl or optionally substituted benzyl, the optionally substituted phenyl or optionally substituted benzyl is optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, —NH—CO—$CH_3$, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion;

with the following provisos:

(1) that when T is —C(=O)($Z_3$), —$CH_2$—N(B)($CH_2$)$_a$—C(=O)($Z^3$), —$CH_2$—N($Z^2$)(C=O)—($CH_2$)$_a$—$Z^3$ or —$CH_2$—N(B)($CH_2$)$_g$—N(B)($CH_2$)$_a$—C(=O)($Z^3$) wherein $Z^3$ is —N($R^1R^2$) where $R^1$ or $R^2$ is a substituted alkyl or substituted cycloalkyl, then the substituent at the 1-position of the substituted alkyl or substituted cycloalkyl cannot be fluoro, chloro or a heteroatom attached substituent; and (2) when any of the substituents defined above which may be a substituted cycloalkyl is a substituted cycloalkyl, then the substituent at the 1-position of the substituted cycloalkyl cannot be fluoro, chloro or a heteroatom attached substituent.

2. A compound or a pharmaceutically acceptable salt thereof of formula (I) according to claim 1 wherein m is 1 and $Z^1$ is H or OH.

3. A compound or a pharmaceutically acceptable salt thereof of formula (I) according to claim 2 wherein T is —$CH_2$—N(B)($CH_2$)$_a$—C(=O)($Z^3$)$_a$—$CH_2$—N($Z^2$)(C=O) —($CH_2$)$_a$—$Z^3$, —$CH_2$—N(B)($CH_2$)$_g$—N(B)($CH_2$)$_a$—C (=O)($Z^3$), —CH=CH—($CH_2$)$_n$—N($Z^4$)($Z^5$), —CH($Z^8$)(N ($Z^6$)($Z^7$)),

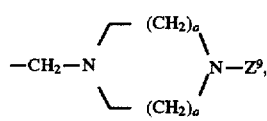

—$CH_2$—N($Z^{12}$)($SO_2Z^{13}$), —$CH_2$—N($Z^{12}$)(C(=O)—$Z^{14}$—$Z^{13}$), —$CH_2$—N($Z^{12}$)($CH_2$)$_g$—N($Z^{19}$)(C(=O)—$Z^{14}$—$Z^{13}$) or —$CH_2$—N($Z^{12}$)($CH_2$)$_g$—N($Z^{15}$)($SO_2$—$Z^{13}$).

4. A compound or a pharmaceutically acceptable salt thereof of formula (I) according to claim 3 wherein T is —CH=CH—(CH$_2$)$_n$—N(Z$^4$)(Z$^5$), —CH(Z$^8$)(N(Z$^6$)(Z$^7$)),

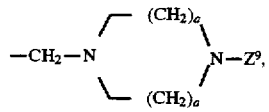

—CH$_2$—N(Z$^{12}$)(SO$_2$Z$^{13}$), —CH$_2$—N(Z$^{12}$)(C(=O)—Z$^{14}$—Z$^{13}$), —CH$_2$—N(Z$^{12}$)(CH$_2$)$_g$—N(Z$^{15}$)(C(=O)—Z$^{14}$—Z$^{13}$) or —CH$_2$—N(Z$^{12}$)(CH$_2$)$_g$—N(Z$^{15}$)(SO$_2$—Z$^{13}$) where Z$^1$ is H.

5. A compound or a pharmaceutically acceptable salt thereof of formula (I) according to claim 4 wherein T is —CH=CH—(CH$_2$)$_n$—N(Z$^4$)(Z$^5$), —CH$_2$—N(Z$^6$)(Z$^7$) or

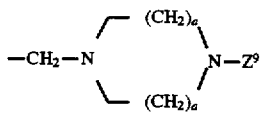

where n is 1; Z$^4$ and Z$^5$ are each independently selected from the group consisting of hydrogen, alkenyl having 3 to 5 carbon atoms provided that the double bond is not adjacent to the nitrogen to which the alkenyl is attached, alkynyl having 3 to 5 carbons provided that the triple bond is not adjacent to the nitrogen to which the alkynyl is attached, hydroxyalkyl having 2 to 4 carbons in the alkyl portion, Q$^{10}$, Q$^{20}$, Q$^{30}$ and alkoxyalkyl having 2 to 4 carbons in the alkyl portion and 1 to 4 carbons in the alkoxy portion, or Z$^4$ and Z$^5$ are taken together with the nitrogen to which they are attached and from Z$^{100}$.

6. A compound or a pharmaceutically acceptable salt thereof of formula (I) according to claim 5 wherein T is —CH$_2$—N(Z$^6$)(Z$^7$) or

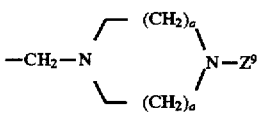

where Z$^6$ is independently selected from the same group of substituents as R$^1$; Z$^7$ is independently selected from the same group of substituents as R$^1$ or is —R$^9$—N(R$^{10}$R$^{11}$); or Z$^6$ and Z$^7$ are taken together with the nitrogen to which they are attached and form Z$^{100}$; and Z$^9$ is amino acyl group, aminoalkyl having 2 to 6 carbons, hydroxyalkyl having 2 to 4 carbons, N-alkylaminoalkyl having 1 to 4 carbons in the alkylamino portion and 2 to 4 carbons in the alkyl portion, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion or —CO—Z$^{14}$—Z$^{13}$.

7. A compound or a pharmaceutically acceptable salt thereof of formula (I) according to claim 6 wherein Q is OH; Z$^1$ is H; T is —CH$_2$—N(Z$^6$)(Z$^7$) where Z$^6$ is hydrogen, methyl or optionally substituted alkyl having 2 to 6 carbon atoms; Z$^7$ is N-alkylaminoalkyl having 1 to 4 carbons in the alkylamino portion and 2 to 4 carbons in the alkyl portion, optionally substituted alkyl having 2 to 6 carbon atoms or optionally substituted cycloalkyl having 3 to 8 carbons; or Z$^6$ and Z$^7$ are taken together with the nitrogen to which they are attached and form pyrrolidino, piperidino 3,4-dehydropiperidino or azabicyclononan-3-yl.

8. A compound or a pharmaceutically acceptable salt thereof of formula (I) according to claim 7 wherein said optionally substituted alkyl of Z$^6$ is propyl; said optionally substituted alkyl of Z$^7$ is propyl, 3-(dimethylamino)-propyl or 2-spirocyclopentyl-hydroxypropyl; and said optionally substituted cycloalkyl of Z$^7$ is cyclohexyl.

9. A compound or a pharmaceutically acceptable salt thereof of formula (I) according to claim 6 wherein Q is OH; Z$^1$ is H; T is —CH$_2$—N(Z$^6$)(Z$^7$) where Z$^6$ hydrogen or methyl; Z$^7$ is methyl, 2-fluoroethyl, 2,2-dimethyl-3-hydroxypropyl, 2-hydroxyethyl, propyl, 3-hydroxypropyl, 2,5-(dihydroxy)cyclohexyl or 3-aminopropyl; or Z$^6$ and Z$^7$ are taken together with the nitrogen to which they are attached and form 4-methylpiperazino, azetidino, 4-hydroxypiperidino, morpholino or 3-hydroxypiperidino.

10. A compound or a pharmaceutically acceptable salt thereof of formula (I) according to claim 6 wherein Q is OH; Z$^1$ is OH; T is —CH$_2$—N(Z$^6$)(Z$^7$) where Z$^6$ is hydrogen; Z$^7$ is 2,2-dimethyl-3-hydroxypropyl; or Z$^6$ and Z$^7$ are taken together with the nitrogen to which they are attached and form hexahydroazepin-1-yl.

11. A compound or a pharmaceutically acceptable salt thereof of formula (I) according to claim 6 wherein the bond between C2–C3 of the macrolide is a double bond, Q is OH; Z$^1$ is OH; T is —CH$_2$—N(Z$^6$)(Z$^7$) where Z$^6$ is hydrogen, methyl or propyl; Z$^7$ is 2,2-dimethyl-3-hydroxypropyl, methyl, propyl or 3-(dimethylamino)propyl; or Z$^6$ and Z$^7$ are taken together with the nitrogen to which they are attached and form hexahydroazepin-1-yl or 3-azabicyclononan-3-yl.

12. A pharmaceutical composition comprising a compound of claim 1 or a pharmaceutically acceptable salt thereof and a pharmaceutically acceptable carrier or diluent.

13. A method of treating a bacterial infection in an animal in need thereof which comprises administering to said animal a bacterial treating amount of a compound of claim 1 or a pharmaceutically acceptable salt thereof.

14. A method of treating a mycoplasmic infection in an animal in need thereof which comprises administering to said animal a mycoplasmic treating amount of a compound of claim 1 or a pharmaceutically acceptable salt thereof.

15. A method of prophylactically treating an animal susceptible to a bacterial or mycoplasmic infection which comprises administering to said animal a prophylactic amount of a compound of claim 1 or a pharmaceutically acceptable salt thereof.

* * * * *